(12) United States Patent
Edgar, Jr. et al.

(10) Patent No.: US 7,991,448 B2
(45) Date of Patent: *Aug. 2, 2011

(54) METHOD, APPARATUS, AND SYSTEM FOR REMOVING MOTION ARTIFACTS FROM MEASUREMENTS OF BODILY PARAMETERS

(75) Inventors: Reuben W. Edgar, Jr., San Antonio, TX (US); August J. Allo, Jr., San Antonio, TX (US); Paul B. Gunneson, Cheshire, CT (US); Jesus D. Martin, Wallingford, CT (US); John R. DelFavero, East Hampton, CT (US); Michael B. Jaffe, Cheshire, CT (US)

(73) Assignee: Philips Electronics North America Corporation, Andover, MA (US)

( * ) Notice: Subject to any disclaimer, the term of this patent is extended or adjusted under 35 U.S.C. 154(b) by 1501 days.

This patent is subject to a terminal disclaimer.

(21) Appl. No.: 11/408,604

(22) Filed: Apr. 21, 2006

(65) Prior Publication Data

US 2006/0258927 A1    Nov. 16, 2006

Related U.S. Application Data

(60) Continuation-in-part of application No. 10/873,758, filed on Jun. 22, 2004, now Pat. No. 7,072,702, which is a division of application No. 10/213,140, filed on Aug. 6, 2002, now Pat. No. 6,810,277, which is a continuation of application No. 09/546,260, filed on Apr. 10, 2000, now Pat. No. 6,519,486, which is a continuation-in-part of application No. 09/410,991, filed on Oct. 1, 1999, now Pat. No. 6,393,311.

(60) Provisional application No. 60/104,422, filed on Oct. 15, 1998.

(51) Int. Cl.
  *A61B 5/1455* (2006.01)
  *A61B 5/02* (2006.01)

(52) U.S. Cl. .................... 600/336; 600/310; 600/502
(58) Field of Classification Search .......... 600/309–344; 356/39, 419
See application file for complete search history.

(56) References Cited

U.S. PATENT DOCUMENTS 4,114,604 A    9/1978  Shaw et al.
(Continued)

FOREIGN PATENT DOCUMENTS

EP    0 303 502 A    2/1989
(Continued)

OTHER PUBLICATIONS

Dowla et al., "Neural Networks and Wavelet Analysis in the Computer Interpretation of Pulse Oximetry Data", Neural Networks for Signal Processing VI—Proc. IEEE, 1996 IEEE Signal Process. Soc., IEEE Workshop, 0-7803-3550-3, 1996.

(Continued)

*Primary Examiner* — Eric F Winakur
*Assistant Examiner* — Chu Chuan Liu

(57) ABSTRACT

A method for removing motion artifacts from devices for sensing bodily parameters and apparatus and system for effecting same that includes analyzing segments of measured data representing bodily parameters and possibly noise from motion artifacts. Each data segment is frequency analyzed to determine up to three candidate peaks for further analysis. Up to three candidate frequencies may be filtered and various parameters associated with each candidate frequency are calculated. A pulse-estimate input may also be accepted from an external source. The best frequency, if one exists, is determined by arbitrating the candidate frequencies and the pulse-estimate input using the calculated parameters according to predefined criteria. If a best frequency is found, a pulse rate and $SpO_2$ may be output. If a best frequency is not found, other, conventional techniques for calculating pulse rate and $SpO_2$ may be used.

20 Claims, 6 Drawing Sheets

U.S. PATENT DOCUMENTS

| | | | |
|---|---|---|---|
| 4,236,527 A | 12/1980 | Newbower et al. | |
| 4,519,396 A | 5/1985 | Epstein et al. | |
| 4,800,495 A | 1/1989 | Smith | |
| 4,819,646 A | 4/1989 | Cheung et al. | |
| 4,859,057 A | 8/1989 | Taylor et al. | |
| 4,860,759 A | 8/1989 | Kahn et al. | |
| 4,863,265 A | 9/1989 | Flower et al. | |
| 4,869,253 A | 9/1989 | Craig, Jr. et al. | |
| 4,892,101 A | 1/1990 | Cheung et al. | |
| 4,911,167 A * | 3/1990 | Corenman et al. | 600/324 |
| 4,942,877 A | 7/1990 | Sakai et al. | |
| 4,955,379 A | 9/1990 | Hall | |
| 4,958,638 A | 9/1990 | Sharpe et al. | |
| 4,960,126 A | 10/1990 | Conlon et al. | |
| 5,025,791 A | 6/1991 | Niwa | |
| 5,058,588 A | 10/1991 | Kaestle | |
| 5,133,013 A | 7/1992 | Munday | |
| 5,190,038 A | 3/1993 | Polson et al. | |
| 5,226,417 A | 7/1993 | Swedlow et al. | |
| 5,299,120 A | 3/1994 | Kaestle | |
| 5,349,952 A | 9/1994 | McCarthy et al. | |
| 5,351,685 A | 10/1994 | Potratz | |
| 5,368,026 A | 11/1994 | Swedlow et al. | |
| 5,368,224 A | 11/1994 | Richardson et al. | |
| 5,372,135 A | 12/1994 | Mendelson et al. | |
| 5,398,680 A | 3/1995 | Polson et al. | |
| 5,400,371 A | 3/1995 | Natarajan | |
| 5,402,778 A | 4/1995 | Chance | |
| 5,431,170 A | 7/1995 | Mathews | |
| 5,440,388 A | 8/1995 | Erickson | |
| 5,448,991 A | 9/1995 | Polson et al. | |
| 5,458,117 A | 10/1995 | Chamoun et al. | |
| 5,459,317 A | 10/1995 | Small et al. | |
| 5,482,036 A | 1/1996 | Diab et al. | |
| 5,490,505 A | 2/1996 | Diab et al. | |
| 5,524,631 A | 6/1996 | Zahorian et al. | |
| 5,533,511 A | 7/1996 | Kaspari et al. | |
| 5,553,614 A | 9/1996 | Chance | |
| 5,553,615 A | 9/1996 | Carim et al. | |
| 5,555,882 A | 9/1996 | Richardson et al. | |
| 5,588,427 A | 12/1996 | Tien | |
| 5,621,730 A | 4/1997 | Kelley | |
| 5,632,272 A | 5/1997 | Diab et al. | |
| 5,645,060 A | 7/1997 | Yorkey | |
| 5,672,875 A | 9/1997 | Block et al. | |
| 5,685,299 A | 11/1997 | Diab et al. | |
| 5,706,202 A | 1/1998 | Itahara et al. | |
| 5,713,355 A | 2/1998 | Richardson et al. | |
| 5,743,263 A | 4/1998 | Baker, Jr. | |
| 5,755,226 A | 5/1998 | Cairm et al. | |
| 5,769,785 A | 6/1998 | Diab et al. | |
| 5,800,348 A | 9/1998 | Kaestle | |
| 5,803,910 A | 9/1998 | Potratz | |
| 5,820,550 A | 10/1998 | Polson et al. | |
| 5,826,222 A | 10/1998 | Griffin | |
| 5,830,137 A | 11/1998 | Scharf | |
| 5,852,638 A | 12/1998 | Chen et al. | |
| 5,853,364 A | 12/1998 | Baker, Jr. et al. | |
| 5,857,462 A | 1/1999 | Thomas et al. | |
| 5,879,294 A | 3/1999 | Anderson et al. | |
| 5,885,213 A | 3/1999 | Richardson et al. | |
| 5,919,134 A | 7/1999 | Diab | |
| 5,934,277 A | 8/1999 | Mortz | |
| 6,002,952 A | 12/1999 | Diab et al. | |
| 6,036,642 A | 3/2000 | Diab et al. | |
| 6,061,582 A | 5/2000 | Small et al. | |
| 6,067,462 A | 5/2000 | Diab et al. | |
| 6,098,038 A | 8/2000 | Hermansky et al. | |
| 6,122,535 A | 9/2000 | Kaestle et al. | |
| 6,157,850 A | 12/2000 | Diab et al. | |
| 6,236,872 B1 | 5/2001 | Diab et al. | |
| 6,393,311 B1 | 5/2002 | Edgar et al. | |
| 6,453,187 B1 | 9/2002 | Prince et al. | |
| 6,519,486 B1 | 2/2003 | Edgar, Jr. et al. | |
| 6,810,277 B2 | 10/2004 | Edgar et al. | |
| 7,072,702 B2 * | 7/2006 | Edgar et al. | 600/336 |

FOREIGN PATENT DOCUMENTS

| | | |
|---|---|---|
| EP | 0 335 357 A2 | 10/1989 |
| EP | 0 226 613 B1 | 9/1993 |
| EP | 0 335 357 B1 | 5/1996 |
| EP | 0 760 223 A1 | 3/1997 |
| EP | 0 791 159 A2 | 3/1997 |
| EP | 0 870 466 A1 | 10/1998 |
| EP | 0 761 159 B1 | 9/1999 |
| EP | 0 682 495 B1 | 12/2001 |
| WO | WO 94/01933 | 1/1994 |
| WO | WO 96/01243 | 5/1996 |
| WO | WO 98/46126 | 10/1998 |
| WO | WO 00/22408 | 4/2000 |

OTHER PUBLICATIONS

Rusch et al., "Signal Processing Methods for Pulse Oximetry", Biol. Med., 1996, pp. 143-159, vol. 26, No. 2.

* cited by examiner

METHOD, APPARATUS, AND SYSTEM FOR REMOVING MOTION ARTIFACTS FROM MEASUREMENTS OF BODILY PARAMETERS

CROSS-REFERENCE TO RELATED APPLICATIONS

This application is a Continuation-In-Part (CIP) of and claims priority under 35 U.S.C. §120 from U.S. patent application Ser. No. 10/873,758 filed on Jun. 22, 2004, which is a Divisional of and claims priority under 35 U.S.C. §120 from U.S. patent application Ser. No. 10/213,140, filed Aug. 6, 2002, now U.S. Pat. No. 6,810,277 B2, issued Oct. 26, 2004, which is a Continuation of and claims priority under 35 U.S.C. §120 from U.S. patent application Ser. No. 09/546,260, filed Apr. 10, 2000, now U.S. Pat. No. 6,519,486 B1, issued Feb. 11, 2003, which is a Continuation-In-Part of and claims priority under 35 U.S.C. §120 from U.S. patent application Ser. No. 09/410,991, filed Oct. 1, 1999, now U.S. Pat. No. 6,393,311 B1, issued May 21, 2002, which claims the benefit of U.S. provisional patent application Ser. No. 60/104,422, filed Oct. 15, 1998, the contents of each of which are expressly incorporated by references into the present application.

BACKGROUND OF THE INVENTION

1. Field of the Invention

This invention relates to the field of signal processing. More particularly, this invention relates to processing measured signals to remove unwanted signal components caused by noise and especially noise caused by motion artifacts. Even more particularly, the invention relates to a method, apparatus and system for removing motion artifacts in the context of a pulse oximeter.

2. Description of the Related Art

The measurement of physiological signals can often be difficult because the underlying physiological processes may generate very low level signals. Furthermore, interfering noise is inherent in the body and the interface between the body and sensors of physiological processes. Examples of physiological measurements include: measurement of electrocardiogram (ECG) signals based on the electrical depolarization of the heart muscle, blood pressure, blood oxygen saturation, partial pressure of $CO_2$, heart rate, respiration rate, and depth of anesthesia. ECG signals, for example, are typically detected by surface electrodes mounted on the chest of a patient. ECG signals are weak at the signal source (i.e., the heart) and are even weaker at the surface of the chest. Furthermore, electrical interference from the activity of other muscles (e.g., noise caused by patient breathing, general movement, etc.) causes additional interference with physiological signals such as an ECG. Thus, considerable care must be taken in the design and use of physiological processors to enhance the quality of the true signal and reduce the effects of interfering noise signals.

It is convenient to characterize a measured signal as being a composite signal composed of a true signal component and a noise signal component. The terms "measured signal" and "composite signal" will be used interchangeably hereinafter. Signal processors are frequently used to remove noise signal components from a composite measured signal in order to obtain a signal that closely, if not identically, represents the true signal. Conventional filtering techniques such as low pass, band pass, and high pass filtering can be used to remove noise signal components from the measured composite signal where the noise signal component occupies a frequency range outside the true signal component. More sophisticated techniques for conventional noise filtering include multiple notch filters, which are suitable for use where the noise signal component exists at multiple, distinct frequencies, all outside the true signal frequency band.

However, it is often the case that the frequency spectrum of the true and noise signal components overlap and that the statistical properties of both signal components change with time. More importantly, there are many cases where little is known about the noise signal component. In such cases, conventional filtering techniques may be ineffective in extracting the true signal.

The measurement of oxygen saturation in the blood of a patient is a common physiological measurement, the accuracy of which may be compromised by the presence of noise. Knowledge of blood oxygen saturation can be critical during surgery. There are means of obtaining blood oxygen saturation by invasive techniques, such as extracting and testing blood removed from a patient using a co-oximeter. But, such invasive means are typically time consuming, expensive, and uncomfortable for the patient. Fortunately, non-invasive measurements of blood oxygen saturation can be made using known properties of energy attenuation as a selected form of energy passes through a bodily medium. Such non-invasive measurements are performed routinely with a pulse oximeter.

The basic idea behind energy attenuation measurements as employed in pulse oximetry is as follows. Radiant energy is directed toward a bodily medium, where the medium is derived from or contained within a patient, and the amplitude of the energy transmitted through or reflected from the medium is then measured. The amount of attenuation of the incident energy caused by the medium is strongly dependent on the thickness and composition of the medium through which the energy must pass, as well as the specific form of energy selected. Information about a physiological system can be derived from data taken from the attenuated signal of the incident energy transmitted or reflected. However, the accuracy of such information is reduced where the measured signal includes noise. Furthermore, non-invasive measurements often do not afford the opportunity to selectively observe the interference causing the noise signal component, making it difficult to remove.

A pulse oximeter is one example of a physiological monitoring system that is based upon the measurement of energy attenuated by biological tissues and substances. More specifically, a pulse oximeter measures the variable absorption caused by blood volume changes, primarily arterial in origin. Pulse oximeters transmit electromagnetic energy at two different wavelengths, for example at 660 nm (red) and 940 nm (infrared, hereinafter IR) into the tissue and measure the attenuation of the energy as a function of time. The output signal of a pulse oximeter is sensitive to the pulsatile portion of the arterial blood flow and contains a component that is a waveform representative of the patient's arterial pulse. This type of signal, which contains a component related to the patient's pulse, is called a plethysmographic waveform or plethysmogram.

The period of rhythmic contraction of the heart by which blood is driven through the aorta and pulmonary artery is known as systole. Maximum light absorbance occurs during the systole of a cardiac cycle and is indicated on a plethysmogram by a low point or systolic valley. Conversely, the period of rhythmic relaxation and dilation of the heart cavities occurs during diastole when blood is drawn into the heart cavities. Minimum light absorbance occurs during the diastole of a cardiac cycle and is indicated on a plethysmogram by a high point or diastolic peak.

Pulse oximetry measurements typically use a digit, such as a finger, or an ear lobe or other element of the body, where blood flows close to the skin as the medium through which light energy is transmitted. The finger, for example, is composed of various tissues and substances including skin, fat, bone, muscle, blood, etc. The extent to which each of these biological tissues and substances attenuate incident electromagnetic energy is generally known. However, the effect of motion can cause changes in the optical coupling of the sensor (or probe) to the finger, the underlying physiology, the local vasculature, optical properties of tissues due to changing optical path length as well as combinations and interactions of all of the above. Thus, patient motion may cause erratic energy attenuation.

A typical pulse oximeter includes a sensor, cabling from the sensor to a computer for signal processing and visual display, the computer and visual display typically being included in a patient monitor. The sensor typically includes two light emitting diodes (LEDs) placed across a finger tip and a photodetector on the side opposite the LEDs. The detector measures both transmitted light signals once they have passed through the finger. The signals are routed to a computer for analysis and display of the various parameters measured.

The underlying physical basis of a pulse oximeter is Beer's law (also referred to as Beer-Lambert's or Bouguer's law) that describes attenuation of monochromatic light traveling through a uniform medium that absorbs light with the equation:

$$I_{transmitted} = I_{incident} \cdot e^{-dc\alpha(\lambda)}, \quad (1)$$

where $I_{transmitted}$ is the intensity of the light transmitted through the uniform medium, $I_{incident}$, is the intensity of incident light, d is the distance light is transmitted through the uniform medium, c is the concentration of the absorbing substance in the uniform medium, expressed in units of mmol $L^{-1}$, and $\alpha(\lambda)$ is the extinction or absorption coefficient of the absorbing substance at wavelength $\lambda$, expressed in units of L/(mmol cm). The properties of Beer's law are valid even if more than one substance absorbs light in the medium. Each light absorbing substance contributes its part to the total absorbance. However, Beer's law does not strictly apply since an LED's output is not monochromatic and scattering effects do have a significant influence. Thus, manufacturers often utilize an empirically determined lookup table to map from the ratio of absorbance (or transmittance) at the red and IR frequencies to a saturation value.

Two LEDs emit narrowband light (i.e., half power bandwidth of typically 15 nm) at two different frequency bands, typically red (centered at about 660 nm) and IR (centered at about 940 nm). The intensity of light transmitted through tissue, $I_{transmitted}$, is different for each wavelength of light emitted by the LEDs. Oxyhemoglobin (oxygenated blood) tends to absorb IR light, whereas deoxyhemoglobin (deoxygenated blood) tends to absorb red light. Thus, the absorption of IR light relative to the red light increases with oxyhemoglobin. The ratio of the absorption coefficients can be used to determine the oxygen saturation of the blood.

To estimate pulsatile blood oxygen saturation, $SpO_2$, a two-solute concentration is assumed. A measure of functional blood oxygen saturation level, $SpO_2$, can be defined as:

$$SpO_2 = 100 \cdot \frac{c_0}{c_r + c_0}, \quad (2)$$

where $c_0$ represents oxyhemoglobin solute concentration, and $c_r$ represents reduced or deoxyhemoglobin solute concentration.

Noise signal components in a measured pulse oximetry light signal can originate from both AC and DC sources. DC noise signal components may be caused by transmission of electromagnetic energy through tissues of relatively constant thickness within the body, e.g., bone, muscle, skin, blood, etc. Such DC noise signal components may be easily removed with conventional filtering techniques. AC noise signal components may occur when tissues being measured are perturbed and, thus, change in thickness while a measurement is being made. Such AC noise signal components are difficult to remove with conventional filtering techniques. Since most materials in and derived from the body are easily compressed, the thickness of such matter changes if the patient moves during a non-invasive physiological measurement. Thus, patient movement can cause the properties of energy attenuation to vary erratically. The erratic or unpredictable nature of motion artifacts induced by noise signal components is a major obstacle in removing them.

Various approaches to removing motion artifacts from measured physiological signals, and particularly for use in pulse oximeters, have been proposed. U.S. Pat. Nos. 5,482,036; 5,490,505; 5,632,272; 5,685,299; 5,769,785; and 6,036,642, all to Diab et al., and U.S. Pat. No. 5,919,134 to Diab, disclose methods and apparatuses for removing motion artifacts using adaptive noise cancellation techniques. The basic proposition behind these Diab et al. patents is to first generate a noise reference signal from the two measured signals, and then use the noise reference signal as an input to an adaptive noise canceller along with either or both of the measured signals to remove the reference noise signal from the measured signals, thus approximating the actual parametric signals of interest. These Diab et al. patents appear to require the use of both measured input signals to generate a noise reference signal. Where the adaptive noise cancellation involves the use of a correlation canceller as disclosed in U.S. Pat. No. 5,482,036, additional problems include significant computational overhead and under certain circumstances, the correlation canceller will drive the output signal to zero.

Another approach to noise artifact elimination is disclosed in U.S. Pat. No. 5,588,427 to Tien. Tien uses fractal dimension analysis to determine the complexity of waveforms in order to determine the proper value of the ratio of true intensities based on signal complexity. The Tien approach employs a fractal analyzer to determine values for two ratios, $\alpha$ and $\beta$, based on the measured time varying intensity of the transmitted red and IR light signals including noise. $\alpha$ is defined as the ratio of the time varying true intensity of light transmitted from the red LED and the time varying true intensity of the light transmitted from the IR LED. $\beta$ is a similar ratio relating the noise introduced during the measurement of the light transmitted by the red LED and the noise introduced during the measurement of the light transmitted by the IR LED. According to Tien, a fractal analyzer then determines values for $\alpha$ and $\beta$ and provides $(\alpha,\beta)$ pairs to a statistical analyzer. The statistical analyzer performs analysis of one or more $(\alpha,\beta)$ pairs to determine the best value for $\alpha$, which is then provided to a look-up table. The look-up table provides a value corresponding to the arterial oxygen saturation in the patient. While the Tien approach appears to be an innovative use of fractal analysis, it also appears to be computationally complex.

Yet another approach to noise artifact elimination is disclosed in U.S. Pat. Nos. 5,885,213; 5,713,355; 5,555,882; and 5,368,224, all to Richardson et al. The basic proposition behind the Richardson et al. approach is to switch operative frequencies periodically based on evaluating the noise level associated with various possible frequencies of operation in order to select the frequency of operation that has the lowest associated noise level. It would appear that data measured at a noisy frequency, using the Richardson et al. approach could be invalid or useless for calculating arterial oxygen saturation. Furthermore, Richardson et al. requires a computational overhead to constantly monitor which frequency of operation provides the least noise.

Another approach to noise artifact elimination is disclosed in U.S. Pat. No. 5,853,364 to Baker, Jr. et al. The Baker, Jr. et al. approach first calculates the heart rate of the patient using an adaptive comb filter, power spectrum and pattern matching. Once the heart rate is determined, the oximetry data is adaptively comb filtered so that only energy at integer multiples of the heart rate are processed. The comb filtered data and the raw oximetry data are filtered using a Kalman filter to adaptively modify averaging weights and averaging times to attenuate motion artifact noise. The adaptive filtering of the Baker, Jr. et al. approach appears to add significant computational complexity to solve the problem of motion artifact rejection.

Still another approach to noise artifact elimination is disclosed in U.S. Pat. No. 5,431,170 to Mathews. Mathews couples a conventional pulse oximeter light transmitter and receiver with a transducer responsive to movement or vibration of the body. The transducer provides an electrical signal varying according to the body movements or vibrations, which is relatively independent of the blood or other fluid flow pulsations. Mathews then provides means for comparing the light signals measured with the transducer output and performing adaptive noise cancellation. An apparent disadvantage of the Mathews approach is the need for a secondary sensor to detect motion.

Still yet another approach to noise artifact elimination is disclosed in U.S. Pat. No. 6,002,952 to Diab et al (hereinafter the '952 patent). Diab et al. recognizes the limitations of adaptive noise cancellation and particularly the use of a correlation canceller. The '952 patent discloses the use of frequency domain analysis to extract a pulse rate from oximetry data. According to the '952 patent, coupling coefficients related to ratios of uncontaminated measurement data and contaminated (noisy) measurement data can be determined from taking the ratios at each of a series of spectral peaks identified in the frequency domain.

The '952 patent further discloses using the coupling coefficients to identify the presence of noise by calculating the difference between the largest and smallest ratio lines for all spectral peaks, determining whether that difference is greater than a pre-selected threshold and whether the frequencies associated with the largest and smallest spectral peaks are arbitrarily close or not to each other. Where noise is detected, a scale factor is used to scrub the measurement data by controlling the gain control input of a gain controlled amplifier. The scale factor is zero in the presence of no noise, and can range up to the largest ratio line where there is noise and the frequencies are not close together. However, the signal scrubbing disclosed in the '952 patent appears to rely on a very limited measure of noise, i.e., whether the difference between the largest and smallest ratio lines is greater than a pre-selected threshold and how close the associated frequencies of largest spectral peak and the smallest spectral peak are relative to one another. It would be preferable to have multiple confidence measures in a method or system for determining physiological parameters in the presence of motion artifacts, e.g., a robust pulse oximeter.

Thus, a need in the art exists for a method, apparatus and system to eliminate motion-induced noise artifacts from light signals, that is relatively simple computationally, and that does not require more than one sensor, does not use correlation cancellers or adaptive noise cancellation and that uses multiple measures of confidence to determine physiological parameters accurately.

SUMMARY OF THE INVENTION

The present invention includes methods, apparatuses and systems for removing noise in physiological measurements caused by motion or other similar artifacts. The methods, apparatuses and systems of the present invention eliminate noise from light signals using a single conventional sensor and are relatively simple computationally.

In accordance with one aspect of the invention, a method of removing motion artifacts from electrical signals representative of attenuated light signals, includes transforming the electrical signals into frequency domain data, identifying a plurality of candidate peaks from the frequency domain data, accepting a pulse-estimate input, analyzing each of the plurality of candidate peaks and the pulse-estimate input in the context of selected parameters calculated with respect thereto and arbitrating between each of the plurality of candidate peaks and the pulse-estimate input based on the selected parameters to select a best frequency.

In accordance with another aspect of the invention, a method of determining pulse rate and saturation from electrical signals representative of attenuated light signals and motion artifacts, includes acquiring a segment of red data and a segment of IR data from each of the electrical signals representative of attenuated light signals, transforming both the segment of red data and the segment of IR data into red and IR frequency domain data, respectively, identifying a plurality of candidate peaks from the red and IR frequency domain data, accepting a pulse-estimate input, analyzing each of the plurality of candidate peaks and the pulse-estimate input in the context of selected parameters calculated with respect thereto, arbitrating between each of the plurality of candidate peaks and the pulse-estimate input based on the selected parameters to select a best frequency, if one exists, outputting pulse rate and saturation from the best frequency, and repeating the above steps for new segments of data. Additionally, various quality or confidence measures may be used to evaluate the validity of the candidates.

A circuit card embodiment includes a processor with memory for storing a computer program that is capable of executing instructions embodying methods of the invention.

A system embodiment includes an input device, an output device, a memory device and a motion artifact rejection circuit card capable of executing instructions stored in the memory device implementing the methods described herein.

Finally, a system embodiment includes an input device, and output device, a memory device and a processor, which may be a digital signal processor, capable of executing instructions stored in the memory device implementing the methods described herein.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

The following detailed description discloses methods, apparatuses and systems for removing motion artifacts from measured plethysmographic waveforms, particularly, but without limitation, those used in pulse oximetry. A system embodiment of the invention includes pulse oximetry hardware and associated software to perform the motion artifact suppression. A method embodiment of this invention includes a series of steps that exploit certain characteristics of plethysmographic waveforms. The methods, apparatuses and systems described below are suitable for use with sensors employing light transmitted or reflected through bodily tissues and substances. For convenience, the following detailed description will assume measurement of light that has been transmitted through a finger of a human. The terms "signal" and "waveform" are used interchangeably herein.

Figure 1:
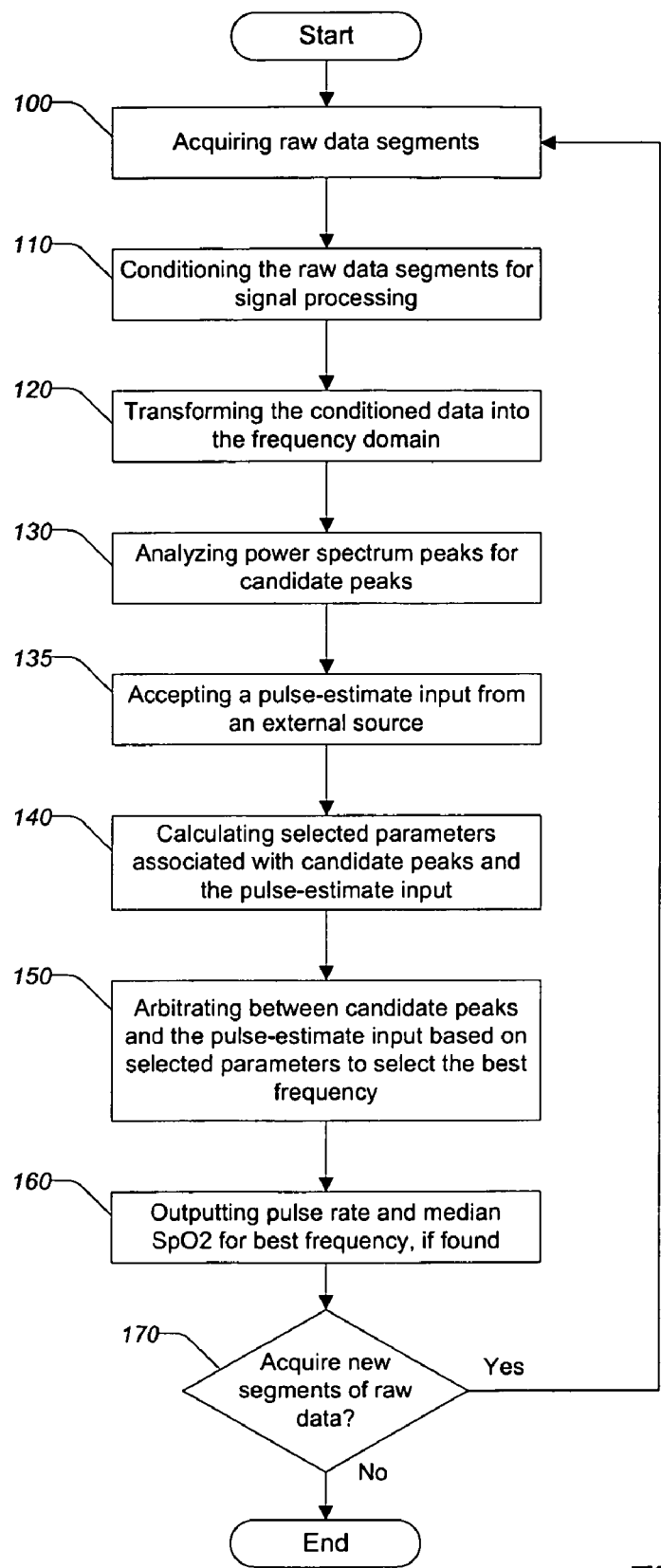
FIG. 1 is a high-level flowchart of a method embodiment of the invention.

FIG. 1 is a high-level flowchart of an embodiment of a method of removing motion artifacts from plethysmographic data and obtaining a measure of pulse rate and $SpO_2$ from that data. The method steps include acquiring segments of raw plethysmographic data 100, both a red data segment and an IR data segment, conditioning each segment of raw data for signal processing 110, transforming the conditioned data into the frequency domain 120, analyzing the frequency domain data for candidate spectral peaks 130, calculating selected parameters associated with the candidate spectral peaks 140, arbitrating between the candidate peaks based on the selected parameters to select a best frequency 150, outputting pulse rate and median $SpO_2$ for the best frequency, if a best frequency was found 160, and repeating these steps for new raw data segments 170, as required. The method embodiment of the invention is applied to both red and IR data signals to eliminate or reduce noise from the data signals prior to outputting pulse rate and $SpO_2$. In the preferred embodiment of the invention, both pulse rate and median $SpO_2$ are output for valid best frequencies.

Figure 2:
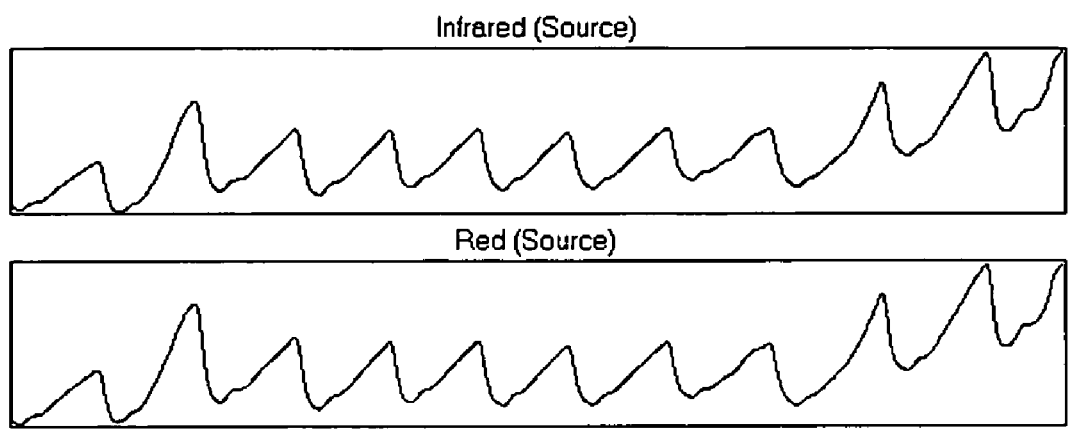
FIG. 2 is two graphs showing acquired IR and red data segments.

The method of this invention begins with acquiring a segment of data (e.g., five or more pulses or approximately ten seconds) measured from a single light source transmitted through a finger and detected with a sensor on the opposite side of the finger. Acquiring a data segment is depicted by block 100 of FIG. 1. FIG. 2 illustrates sample segments of IR and red data acquired according to block 100 of FIG. 1. The horizontal axis of FIG. 2 is measured in units of time, and specifically here in seconds. The vertical axis of FIG. 2 is measured in arbitrary units, and specifically here in analog-to-digital output units. For convenience, a 10.24 second segment of data will be used to illustrate the method. A 10.24 second segment of data corresponds to 1024 data points with a sampling rate of 100 data points per second. It should be readily apparent to one of ordinary skill in the art that the method of the invention is not limited to data segments of this size. The signal processing steps described herein may be performed on both red and IR data segments independently and simultaneously. Thus, while the steps of the method may be illustrated with data from an IR light signal, the same steps are applicable to data from a red light signal and vice versa. The terms "data segment," "input waveform," "data signal" and "signal" are used interchangeably herein.

A segment of data may be received from a sensor that converts transmitted or reflected light signals into electrical signals. U.S. Pat. Nos. 5,190,038; 5,398,680; 5,448,991; and 5,820,550 to Polson et al., the disclosures of each of which are incorporated herein by reference, disclose and claim electronic systems for receiving red and IR data from a sensor, pre-conditioning the electrical signals and then converting the pre-conditioned electrical signals into digital data using an analog-to-digital converter for subsequent digital signal processing. The raw red and IR waveforms may be sampled at any convenient data rate. However, for simplicity of illustration, a sampling rate of 100 Hz will be assumed. Additionally, pulse rate and $SpO_2$ may be calculated on any convenient periodic or non-periodic basis. However, again for simplicity, we will assume that pulse rate and $SpO_2$ are calculated on a periodic basis every ½ second.

Figure 3:
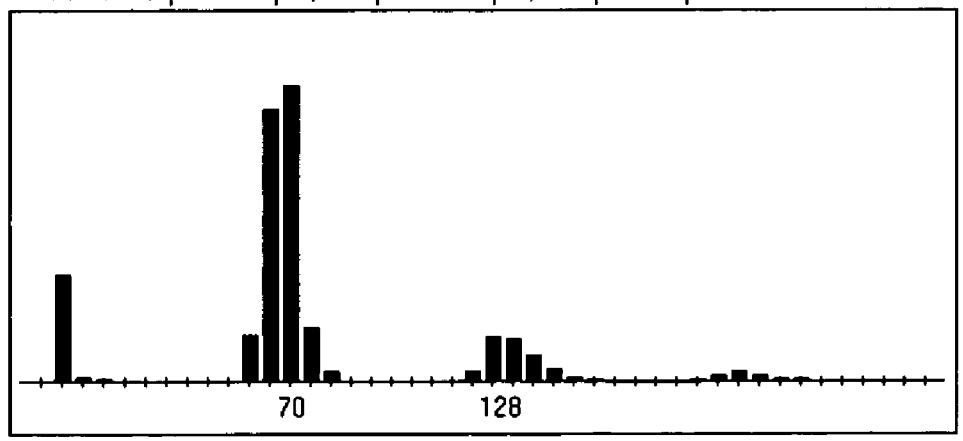
FIG. 3 is a graph of the power spectrum of the IR data segment in FIG. 2 in accordance with the invention.

Once a segment of data from a single electrical signal, i.e., red or IR, has been acquired and digitized, it may be conditioned for subsequent signal processing as depicted by block 110 of FIG. 1. Signal conditioning may include filtering to reduce spectral leakage resulting from subsequent frequency analysis. There are several window filters that may be suitable for such purposes. For example, and not by way of limitation, a Hanning window may be used to reduce spectral leakage. It will be readily apparent to one of ordinary skill in the art of digital signal processing that other window filters and methods of filtering data to reduce spectral leakage may be selected. As such methods of filtering and various filters are known to one of ordinary skill in the art of signal processing, they will not be further detailed herein. FIG. 3 illustrates the power spectrum of the IR data segment of FIG. 2 after filtering. The vertical axis of FIG. 3 may be measured in any arbitrary units of power. The horizontal axis is measured in any units of frequency, specifically here in units of bpm.

The conditioned data is then transformed into the frequency domain for further analysis and signal processing, see block 120 of FIG. 1. Signal processing as described herein is generally performed in the frequency domain. The segment of data is converted into the frequency domain by, for example, performing the conventional Fast Fourier Transform (FFT) on the data segment. FIG. 3 is a graph of the FFT of the IR data segment of FIG. 2. FIG. 3 illustrates a primary candidate peak at a frequency of approximately 70 bpm and a secondary candidate peak at a frequency of approximately 128 bpm.

Other common techniques of converting time-domain data to the frequency domain may also be used, e.g., classical methods using the FFT, such as the periodogram or correlogram, autoregressive methods, Prony's method, minimum variance methods, and maximum likelihood methods. Additionally, time domain data may be converted to the frequency domain using transforms such as discrete cosine transform, wavelet transform, discrete Hartley transform, and Gabor transform. The preferred transform according to this method is the FFT with a window size of 1024 points. The 1024 data points are placed in a buffer, the FFT buffer. The FFT transforms the 1024 points of data from the time domain into the frequency domain. The output of the FFT is 512 points of real and 512 points of imaginary data in the frequency domain. From these 512 points of real and 512 points of imaginary data the power spectrum is calculated and placed in a power spectrum buffer.

Both transient and periodic noise artifacts can induce peaks in the frequency domain that may be larger than the peak associated with the patient's heart rate. The frequency peak that actually represents the patient's heart rate (best frequency) must then be determined. Analyzing the power spectrum peaks to determine candidate spectral peaks is depicted in block 130 of FIG. 1. One approach to determining the best frequency would be to order the frequencies by peak amplitude from largest to smallest, $F_1$ to $F_n$, where $F_1$ through $F_n$ are not harmonics of each other, and analyze them one by one to find the correct frequency, i.e., the patient's heart rate. However, a preferred method selects up to three candidate spectral peaks for further analysis.

The function of block 130 is to locate candidate spectral peaks from the power spectrum computed in block 120. The power spectrum buffer is an array of 512 vector points (referred to herein as "bins") in the frequency domain. Each array element in the power spectrum buffer represents the power of the corresponding frequency in the original raw data waveform. Of the 512 bins, only bins 5 (29 bpm) through 43 (252 bpm) are of interest, since this range covers the physiological limits of the human heart rate. All other bins are unused by the method of the invention because they cannot Physiologically represent a valid spectral frequency of a pulse rate. Table 1, below, Shows the first 45 points of the power spectrum array.

TABLE 1

| Power Spectrum Buffer bin number n | Frequency (Hz) f = n * 100/1024 | Pulse Rate (bpm) Pulse Rate = f * 60 |
|---|---|---|
| 0 | 0.00000 | 0.0 |
| 1 | 0.09766 | 5.9 |
| 2 | 0.19531 | 11.7 |
| 3 | 0.29297 | 17.6 |
| 4 | 0.39063 | 23.4 |
| 5 | 0.48828 | 29.3 |
| 6 | 0.58594 | 35.2 |
| 7 | 0.68359 | 41.0 |
| 8 | 0.78125 | 46.9 |
| 9 | 0.87891 | 52.7 |
| 10 | 0.97656 | 58.6 |
| 11 | 1.07422 | 64.5 |
| 12 | 1.17188 | 70.3 |
| 13 | 1.26953 | 76.2 |
| 14 | 1.36719 | 82.0 |
| 15 | 1.46484 | 87.9 |
| 16 | 1.56250 | 93.8 |
| 17 | 1.66016 | 99.6 |
| 18 | 1.75781 | 105.5 |
| 19 | 1.85547 | 111.3 |
| 20 | 1.95313 | 117.2 |
| 21 | 2.05078 | 123.0 |
| 22 | 2.14844 | 128.9 |
| 23 | 2.24609 | 134.8 |
| 24 | 2.34375 | 140.6 |
| 25 | 2.44141 | 146.5 |
| 26 | 2.53906 | 152.3 |
| 27 | 2.63672 | 158.2 |
| 28 | 2.73438 | 164.1 |
| 29 | 2.83203 | 169.9 |
| 30 | 2.92969 | 175.8 |
| 31 | 3.02734 | 181.6 |
| 32 | 3.12500 | 187.5 |
| 33 | 3.22266 | 193.4 |
| 34 | 3.32031 | 199.2 |
| 35 | 3.41797 | 205.1 |
| 36 | 3.51563 | 210.9 |
| 37 | 3.61328 | 216.8 |
| 38 | 3.71094 | 222.7 |
| 39 | 3.80859 | 228.5 |
| 40 | 3.90625 | 234.4 |
| 41 | 4.00391 | 240.2 |
| 42 | 4.10156 | 246.1 |
| 43 | 4.19922 | 252.0 |
| 44 | 4.29688 | 257.8 |

In table 1, column 1 is the bin number, n; column 2 is the center frequency, f, of the corresponding bin number, n, calculated as the product of the bin number and sampling rate (100 samples/sec) divided by the block size used by the FFT (i.e., 1024); and column 3 is the pulse rate corresponding to the center frequency, f, of column 2, calculated by multiplying f (measured in units of beats per second) by 60 to convert to units of beats per minute.

In order to select candidate peaks (and corresponding frequencies), different amplitude analysis methods are applied to different frequency bands. The amplitude of adjacent and nearby frequency components of the candidate peak amplitude may be compared in terms of their absolute or relative values. For example, the frequencies represented by candidate bins 5 through 10 ("5-10" search method) may be stepped through in a sequential fashion. According to the "5-10" search method, a candidate bin is assumed to be a candidate power spectrum peak if the previous three bins and subsequent four bins relative to a candidate bin are all lower in power than the candidate bin. For example, in order for bin 6 to be a candidate spectral peak, bins 3, 4, 5, 7, 8, 9 and 10 must all be lower in power than bin 6. The terms "spectral peak," "power peak," or simply "peak" are used synonymously herein. Various amplitude, shape, syntactic or other pattern analysis methods may be applied to identify a candidate peak. Also, multiple curve fit methods, as known to one of ordinary skill in the spectroscopic analysis, may also be applied.

Once all possible power spectrum peak candidates are found, predetermined criteria are applied to select, at most, three candidate spectral peaks. First, the power peak associated with the largest power amplitude is selected to be the primary candidate peak. Then, any power peaks that are determined to be harmonics of the primary candidate power peak are eliminated. According to the method, a harmonic is defined as any power peak the frequency of which is a multiple of the primary peak, ±1 bin, and the amplitude of which is less than half the maximum allowed power of the previous harmonic, or in the case of the first harmonic, less than half the power of the primary peak. For example, assume a primary candidate peak is found at bin 10. Possible harmonic bins of 10 are bins 19-21, 29-31 and 39-41. Continuing with the example, if the primary power peak amplitude (bin 10) is 100 arbitrary power spectrum units, then bins 19-21 must be less than 50 units to be deemed a harmonic, bins 29-31 must be less than 25 units and bins 39-41 must be less than about 12 units, where units are the measure of the amplitude of the power spectrum. Other weights may be applied to the analysis of the sequence for detection of harmonics of the candidate spectral peak without departing from the scope of the invention.

After harmonics of the primary candidate peak are eliminated, the next largest remaining power peak found (if any) is selected to be the secondary candidate peak. Finally, if the previous pulse rate is non-zero, the power spectrum corresponding to the previous pulse rate is determined. If the bin corresponding to the previous pulse rate is not equal to the primary or secondary candidate power peak, then the bin corresponding to the previous pulse rate is selected to be the tertiary candidate peak. Thus, up to three candidate peaks (primary, secondary and tertiary) and corresponding frequencies of each candidate peak are identified in block 130 of FIG. 1.

Block 135 of FIG. 1 depicts accepting a pulse-estimate input from an external source. The pulse-estimate input formats and sources are explained more fully below in the discussion of FIGS. 7-9. Occasionally, the noise spectra from the Red and IR sensors may be close enough to the actual heart rate such that distinguishing the actual heart rate from the noise spectra may be difficult. For example, in some cases, the noise spectra may have a high enough peak to be selected as the secondary candidate peak, or if the noise spectra has the highest peak, as the primary candidate peak. In such cases, accepting a pulse-estimate input from an externally determined heart/pulse rate source and incorporating this pulse-estimate input with the other candidate peaks as a potential pulse rate may produce a more accurate best frequency for the pulse rate.

Figure 6:
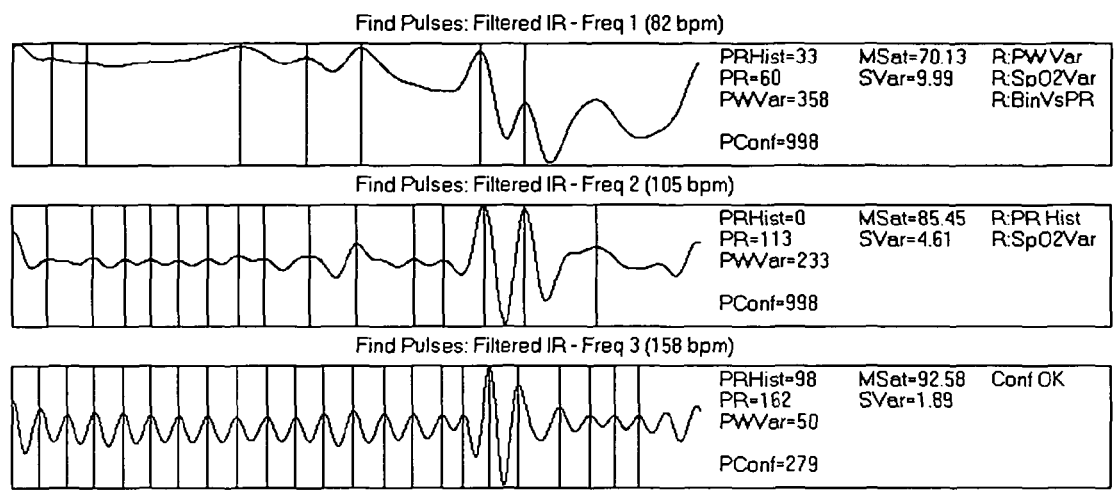
FIG. 6 illustrates three graphs of IR data after filtering with three different IR filters and segmented with vertical lines to show pulses and parameter calculations according to the invention.
Figure 6A:
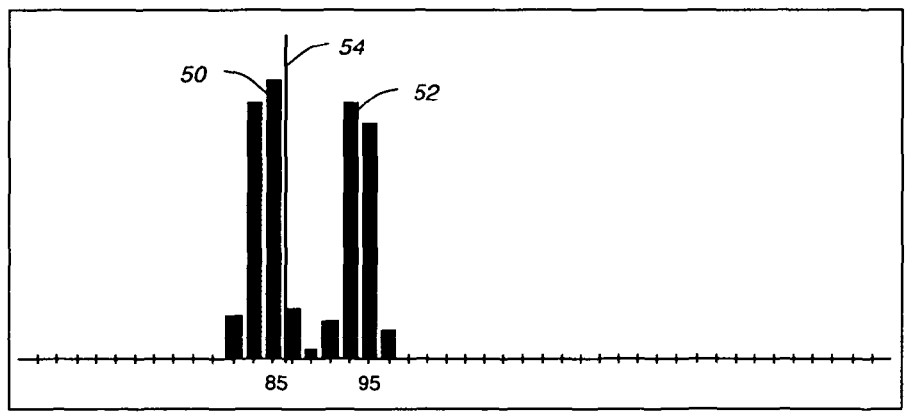
FIG. 6A illustrates a graph of a frequency domain transformed IR signal, showing candidate peaks and a pulse-estimate input.

By way of example, and not limitation, FIG. 6A illustrates a graph of a frequency domain transformed IR signal, showing a candidate peak 50 at approximately 82 bpm representing the actual pulse rate, and another candidate peak 52 at approximately 95 bpm representing a noise artifact. Line 54 illustrates a pulse-estimate input of about 85 bpm, which was input from the external source. Thus, in the example of FIG. 6A, when noise artifacts overlap with the actual pulse rate, or mask the actual pulse rate, the pulse-estimate input may provide a best frequency for the pulse rate rather than one of the candidate peaks.

Figure 6B:
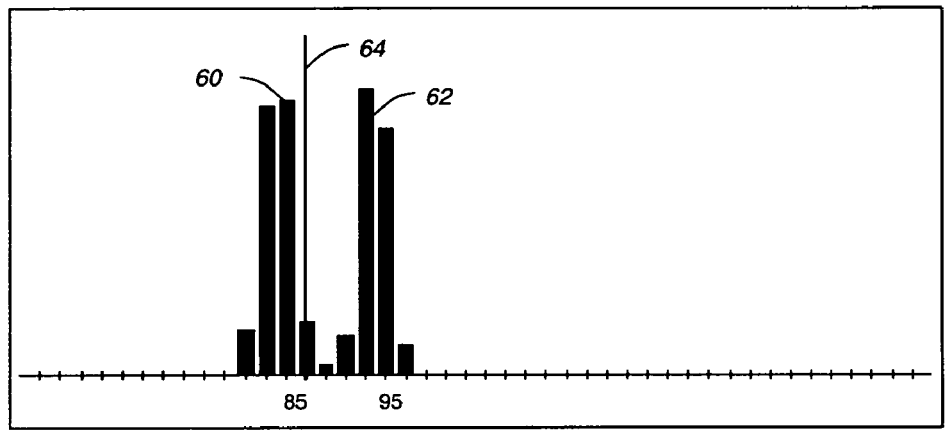

Similarly, FIG. 6B illustrates a graph of a frequency domain transformed IR signal, showing a candidate peak 60 at approximately 82 bpm representing the actual pulse rate, and another candidate peak 62 at approximately 95 bpm representing a noise artifact. Line 64 illustrates a pulse-estimate input of about 85 bpm, which was input from the external source. In the example of FIG. 6B, the noise artifact peak 62 is actually higher than candidate peak 60. In such a case, the pulse-estimate input may provide a better estimate for the pulse rate rather than one of the candidate peaks.

Of course, the pulse-estimate input may also include inaccuracies. Therefore, embodiments of the present invention may provide a confidence factor for the pulse-estimate input and other confidence factors for the primary, secondary, and tertiary candidate peaks in selecting the best estimate of the current pulse rate. With the confidence factors, embodiments of the present invention may adapt to different accuracy levels for different pulse-estimate inputs. Furthermore, embodiments of the present invention may combine the pulse-estimate input with one or more of the candidate peaks with data fusion techniques to arrive at a more accurate estimate of the current pulse rate. For example, in FIG. 6A, the candidate peak 50 at approximately 82 bpm may be combined with the pulse-estimate input 54 of about 85 bpm to arrive at an estimated pulse rate between 82 and 85 bpm.

Returning to FIG. 1, block 140 depicts calculating selected parameters associated with the candidate peaks identified in block 130 and the pulse-estimate input from block 135. Block 140 may include pulse window filtering, and calculating such parameters as peak detection, pulse rejection criteria and descriptive parameters associated with each of the up to three candidate power peaks found from block 130. These parameters are used to determine a pulse confidence for each candidate peak. The parameters calculated according to the invention for each filtered candidate peak include measures of central tendency and variability of pulse width, pulse rate and $SpO_2$, as well as measures of the history and confidence of these parameters. A exemplary embodiment of the present invention includes parameters such as: (1) Window Pulse Rate, (2) Pulse Width Variability, (3) $SpO_2$ Variability, (4) Pulse Window $SpO_2$, (5) Pulse Peak Amplitude Variability, (6) Pulse Rate History Percentage, and (7) Pulse Window Confidence. It should be noted that other parameters including, but not limited to, other measures of central tendency, variability (i.e., skewness, kurtosis), history/trend and confidence, could be calculated from the candidate power peaks without departing from the scope of the invention. Each of the parameters listed is discussed in greater detail below, beginning with pulse window filtering.

Prior to calculating the aforementioned parameters, each candidate peak may be filtered with a narrow band filter, such as a narrow band pass, finite impulse response (FIR) filter. In one aspect of the present invention, one of several predefined FIR filters is applied to a given bin or candidate peak. The peak frequencies of the filters may be separated by a fixed difference in frequency (measured in Hz or bpm), such as 25 bpm, or may be variable and a function of either frequency or a characteristic of the spectrum, for example variability or noise, or both. For example, if a candidate peak was found at bin 12, a filter with center or peak frequency of 76.2 bpm might be chosen. A fixed difference in frequency may be in a range from about 15 bpm to about 40 bpm. Likewise, a variable difference in frequency may be in a range from about 15 bpm to about 40 bpm.

Preferably, to improve discrimination, especially with closely spaced peaks, the band pass filter coefficients may be stored or generated and adjusted as needed so that the center frequency is nearly identical to the candidate frequency. Additionally, other filtering methods such as (a) other types of band pass filters, i.e., infinite impulse response (IIR) filters, and (b) frequency domain methods such as transforming the data into the frequency domain (for example, FFT), filtering or eliminating unwanted components in the frequency domain and transforming back into the time domain (for example, inverse FFT) for further signal processing, may be applied.

Once the up to three peak candidates are selected and filtered, a peak detector algorithm is applied to each of the up to three candidate peaks in the time domain. The function of the peak detector algorithm is to identify power spectrum peaks in each of the filtered time domain data segments and their associated center frequencies. The terms "window" and "pulse window" are used interchangeably with "time domain data segment" herein. For each peak found in the time domain, the pulse width is calculated as the time between each peak. The Window Pulse Rate is calculated by dividing the sum of the pulse width time of all peaks by the number of peaks detected.

Pulse Width Variability, a measure of how consistent the pulse width is for all the peaks in a given pulse window, is calculated according to the method of the invention. With the exception of subjects presenting cardiac arrhythmias, particularly ventricular arrhythmias, the variability of the pulse width of all the peaks should be low within a short time interval such as a 10.24 second window. Higher pulse width variability often is an indication of either (a) cardiac arrhythmias or (b) physiological artifacts such as motion. Pulse Width Variability is calculated as the sum of absolute differences between individual pulse widths and the average pulse width normalized by the average pulse width:

$$\text{Pulse Width Variability} = \frac{\sum_i |\text{Average Pulse Width} - \text{Pulse Width}_i|}{\text{Average Pulse Width}}, \quad (3)$$

where, i is the number of peaks detected in the window, Pulse Width$_i$ is the pulse width for the ith peak, and Average Pulse Width is the sum of the individual pulse widths divided by the number of pulses. For example, a pulse rate of 180 bpm has a pulse width of 330 ms; and a pulse rate of 60 bpm has a pulse width of 1000 ms. If an average pulse width difference was found to be 100 ms, this would have a much greater effect at 180 bpm than 60 bpm. Thus, dividing by the pulse rate normalizes the pulse width variability. Returning to the 180 bpm versus 60 bpm example, dividing by the Average Pulse Width causes the Pulse Width Variability to be 3 times greater at 180 bpm than at 60 bpm.

SpO$_2$ is calculated for each peak in the pulse window using the ratio, R, which is "mapped" to SpO$_2$ via a lookup table. This ratio, R, is defined as:

$$R = \frac{\left(\frac{\text{Red } AC \text{ Component}}{\text{Red } DC \text{ Component}}\right)}{\left(\frac{IR \; AC \text{ Component}}{IR \; DC \text{ Component}}\right)}, \quad (4)$$

The ratio, R, in equation 4 is used to index into an empirically derived table to determine SpO$_2$. The IR AC Component is chosen at the point of maximum negative slope between the peak and valley for each peak of the filtered IR waveform. The red AC Component is the slope of the filtered red waveform at the time coincident with the above selected IR AC Component. The peak and valley points from the IR filtered waveforms are transposed onto the raw red and IR waveform. The average between the peak and the valley is considered the DC component (analogous to a DC offset for a positively biased AC waveform). This DC component is calculated for both the red and IR waveforms (i.e., red DC Component and IR DC Component). This process is repeated for each of the up to three band pass filtered pulse windows corresponding to the candidate peaks identified in block 130 of FIG. 1. The term "pulse window" is used herein to represent time domain data corresponding to a particular candidate peak that has been band pass filtered.

SpO$_2$ Variability, a measure of how consistent the SpO$_2$ is for all the peaks in a pulse window, is calculated according to the method of the invention. Under typical conditions, SpO$_2$ Variability is low, often within ±2 percent saturation over a short time interval such as the 10.24 second pulse window. When the pulse window is filtered by a frequency that is not related to the pulse rate (e.g., random noise), the SpO$_2$ Variability tends to be high. Therefore, SpO$_2$ Variability is a good measure for determining confidence in a pulse window. SpO$_2$ Variability is calculated as the sum of the absolute difference between the individual SpO$_2$ values and the average SpO$_2$ for the pulse window.

$$SpO_2 \text{ Variability} = \sum_i |\text{Average } SpO_2 - SpO_{2,i}|, \quad (5)$$

where i is the number of peaks detected in the window, and SpO$_{2,i}$ is the saturation calculated for the ith peak detected and Average SpO$_2$ is sum of the individual SpO$_2$ values divided by the number of individual SpO$_2$ values.

The Pulse Window SpO$_2$ is calculated by the method of the invention as the median value of all of the SpO$_2$ values within the current pulse window. Other methods of determining central tendency may be used including, but not limited to, a weighted mean or average.

The Pulse Peak Amplitude Variability, a measure of the consistency of the amplitude of the pulse peaks in a pulse window, is calculated according to the method of the invention. Pulse Peak Amplitude Variability is calculated as the sum of the differences between the individual pulse peak amplitudes and the average pulse peak amplitude for the pulse window.

Motion artifacts are usually not purely rhythmic in nature. Therefore, the portion of the power spectrum comprising motion artifacts changes dynamically as the spectrum of the motion artifacts changes. In contrast, the spectrum of the underlying pulse rate varies much less over longer periods of time relative to motion artifact spectrum.

Pulse Rate History Percentage, another parameter useful for detecting motion artifacts, is calculated by the method of the invention. According to the method, a pulse rate is calculated for the primary and secondary candidate peaks and these pulse rate calculations are saved in memory. This memory may be any capacity but preferably is capable of storing at least between 10-60 seconds of pulse rates (for the primary and secondary candidate peaks) and is updated periodically with the newest values overwriting the oldest values. For illustration purposes, assume the memory stores 30 seconds of pulse rates for the primary and secondary peaks. Pulse Rate History Percentage is calculated according to the method of the invention as the percentage that the pulse rate corresponding to the candidate peak occurred in a given period of time, e.g., the most recent 30 seconds. Of course, one of ordinary skill in the art may recognize that a Pulse Rate History Percentage may be calculated in other analogous ways. For example, there could be a longer history of pulse rates (i.e., more or less than 30 seconds) and it could be weighted or filtered in various manners without departing from the scope of the invention.

A pulse window under evaluation may be rejected from further processing and flagged as an invalid pulse window if certain criteria are met. A pulse window under evaluation may be checked against the following criterion:
1. The number of peaks in the pulse window, i, is two or less (i #2)
2. The Window Pulse Rate is zero (i.e., no frequency found) .\

Additional criteria related to variability and history may include the following:
1. The Pulse Rate History Percentage is less than a percentage of a significant portion of the pulse. According to the preferred embodiment of the invention, a percentage of a significant portion of the pulse would be in the range from about 25% to about 30%.
2. The $SpO_2$ Variability is greater than "normal" variation in $SpO_2$ in either absolute or relative terms. According to the preferred embodiment of the invention, $SpO_2$ Variability greater than a threshold ranging from about 3% to about 5% is greater than "normal" variation in $SpO_2$.
3. The Pulse Width Variability is greater than a threshold representing excessive variations. According to the preferred embodiment of the invention, a threshold representing excessive variations may fall within the range of about 200 to about 400 points for a pulse window of 1024 points.
4. The Window Pulse Rate differs by more than an excessive amount either in absolute or relative terms from the center frequency of the candidate power spectrum peak. According to the preferred embodiment of the invention, an excessive amount is a threshold greater than about 20 bpm to about 30 bpm, or about 20% to about 35% of the center frequency, whichever maximum threshold is smaller.

If the pulse window under evaluation meets any of these criteria, then the pulse window under evaluation is rejected as invalid and flagged as such. Also, the optimal thresholds and values for each of the above criteria may be optionally adjusted by methods known to one of ordinary skill in the art, including but not limited to, learning or search methods.

A confidence measure, Pulse Window Confidence, is also calculated according to block 140 of FIG. 1. According to the preferred method of the invention, Pulse Window Confidence is calculated as a weighted sum of the Pulse Width Variability, $SpO_2$ Variability, Pulse Amplitude Variability and the Pulse Rate History Percentage parameters. The lower the value of Pulse Window Confidence measure, the higher the confidence that the candidate peak under evaluation is a valid pulse rate. The Pulse Window Confidence, which is a point value without units, is only computed for each of the up to three remaining candidate peaks and then passed to the arbitrating step, see block 150 of FIG. 1.

Depending on how the pulse-estimate input is acquired, which is explained more fully below in the discussion of FIGS. 7-9, some of the selection parameters may also be used on the pulse-estimate input. For example, if the pulse estimate input is a time-domain representation of a pulse/heart rate from an external source, the selection parameters and signal processing operation for (1) Window Pulse Rate, (2) Pulse Width Variability, (5) Pulse Peak Amplitude Variability, and (6) Pulse Rate History Percentage, may be equally applicable to the pulse-estimate input.

The function of the arbitrating step, block 150 of FIG. 1, is to determine which, if any, of the up to three candidate peaks or the pulse-estimate input should be accepted. The arbitrating step 150, is accomplished by evaluating the calculated parameters, including the confidence or quality measures, (i.e., Pulse Window Confidence), of the candidate peaks relative to one another. Some of the candidate peaks may already have been flagged as an invalid pulse window, and thus, are not evaluated further. If none of the up to three candidate peaks is valid, no new pulse rate or new saturation will be displayed according to the method of the invention. Alternatively, if none of the up to three candidate peaks are valid, another algorithm (other than the method of the invention) may be employed to determine the pulse rate and saturation, see for example U.S. Pat. Nos. 5,190,038; 5,398,680; 5,448,991; and 5,820,550 to Polson et al. Arbitration is then conducted among the up to three remaining candidate peaks in order to determine which, if any candidate peak, should be selected as the best frequency. The arbitration is preferably executed in the sequence presented below.

1. If the pulse-estimate input is valid, then it should be selected as the best frequency.
2. If the primary candidate peak frequency, f1, is zero, then there is no valid candidate peak (i.e., no best frequency).
3. If the tertiary candidate peak Pulse Window Confidence is less than the Pulse Window Confidence for either the primary candidate peak or the secondary candidate peak, then the tertiary candidate peak is the best frequency. Recall that the lower the Pulse Window Confidence value, the higher the confidence that the candidate peak is the true pulse rate.
4. If the primary candidate peak and the secondary candidate peak have both been rejected, then there is no valid candidate peak (i.e., no best frequency).
5. If the primary candidate peak has not been rejected and the secondary candidate peak has been rejected, then the primary candidate peak is the best frequency.
6. If the primary candidate peak has been rejected and the secondary candidate peak has not been rejected, then the secondary candidate peak is the best frequency.
7. If the primary candidate peak Pulse Window Confidence is greater than the secondary candidate peak Pulse Window Confidence by a specified threshold, $t_1$, and the primary candidate peak Pulse Rate History Percentage is greater than another specified threshold, $t_2$, then the primary candidate peak is the best frequency. Similar criteria apply if the secondary candidate peak Pulse Window Confidence is greater than the primary candidate peak.
8. If the secondary candidate peak frequency, $f_2$, is a rough harmonic of the primary candidate peak frequency, $f_1$, and the Pulse Window Confidence of the primary candidate peak is not more than a specified number of points greater than the Pulse Window Confidence of the secondary candidate peak, then accept the primary candidate peak. Secondary candidate peak frequency, $f_2$, is a rough harmonic of the primary candidate peak frequency, $f_1$, if the candidate frequency is within a frequency tolerance of approximately ±10 bpm. Again, similar criteria apply if the secondary candidate peak is a rough harmonic of the primary candidate peak.
9. If the Pulse Window Confidence of the primary candidate peak is no more than a specified number of points greater than the Pulse Window Confidence of the secondary candidate peak, then accept the primary candidate peak. Otherwise, accept the secondary candidate peak.

Once a candidate peak or the pulse-estimate input has been accepted (as the best frequency) according to the arbitrating step 150, the pulse rate and $SpO_2$ are calculated for the best frequency and output, for example, to a display or monitor, as depicted in block 160 of FIG. 1. The steps 100-160 may then be repeated for any new segments of data as depicted in decision block 170 of FIG. 1. The above sequence is exemplary only, and not intended to be limiting. Furthermore, one of ordinary skill in the art will recognize that the various criteria selected to evaluate pulse shape may be assigned weights to emphasize relative importance.

Figure 4:
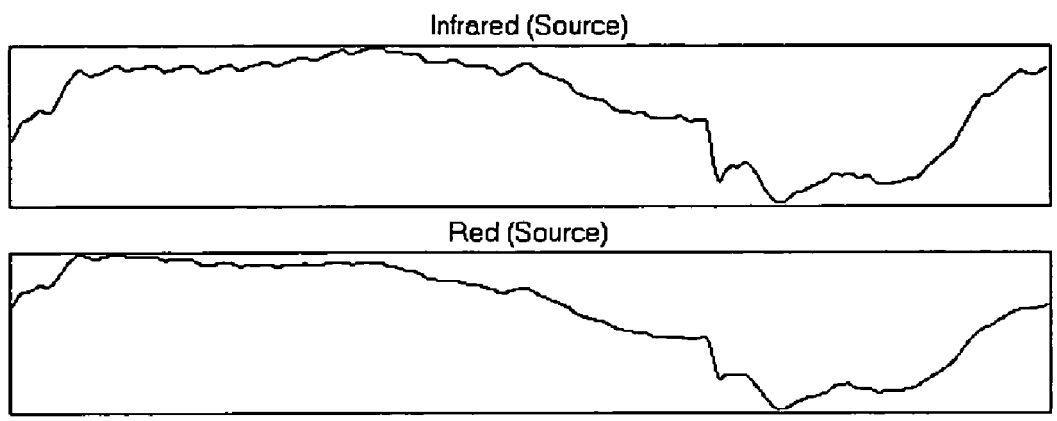
FIG. 4 illustrates example graphs of measured IR and red data segments in accordance with the invention.
Figure 5:
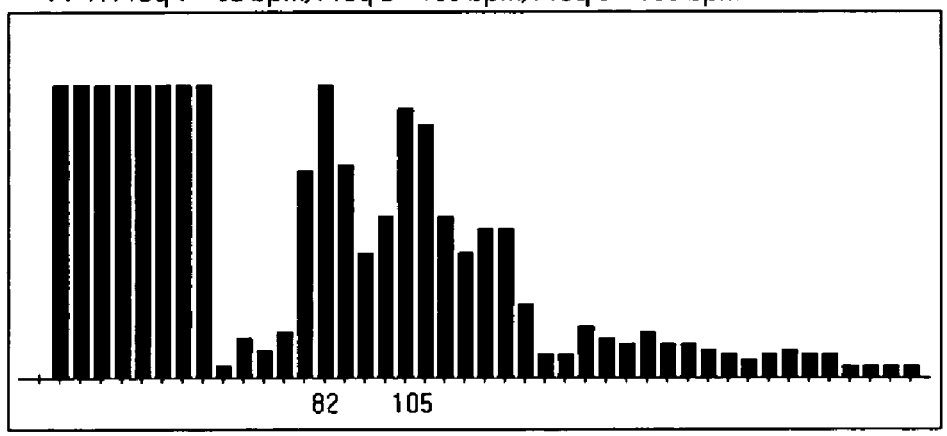
FIG. 5 is a graph of the frequency domain transformed IR signal from FIG. 4.

FIGS. 4-6 illustrate exemplary graphical results from application of the preferred method of the invention. FIG. 4 shows graphs of measured IR and red data segments in accordance with the invention. FIG. 5 is a graph of the frequency domain transformed IR signal from FIG. 4, showing a primary candidate peak at approximately 82 bpm, a secondary candidate peak at approximately 105 bpm.

FIG. 6 illustrates three graphs of IR data after filtering with three different FIR filters and segmented with vertical lines to delineate pulses and parameter calculations according to the invention. The parameter calculations displayed to the right in the graphs shown in FIG. 6 are exemplary only, and are not necessary for practicing the invention. With respect to those parameter calculations displayed, "PRHist" corresponds to Pulse Rate History Percentage; "PR" corresponds to Window Pulse Rate; "PWVar" corresponds to Pulse Width Variability; "MSat" corresponds to Pulse Window SpO2; "SVar" corresponds to $SpO_2$ Variability; "Pconf" corresponds to Pulse Window Confidence; "Conf OK" corresponds to an accepted candidate peak or the best frequency, and "R:xxxx" corresponds to a notation that the candidate peak under evaluation has been rejected for the reason "xxxx," i.e., a parameter calculation has concluded with a rejection of the candidate peak all as disclosed herein.

The top graph in FIG. 6 represents the pulse window corresponding to the primary candidate peak at approximately 82 bpm as shown in FIG. 5. The middle graph in FIG. 6 represents the pulse window corresponding to the secondary candidate peak at approximately 105 bpm as shown in FIG. 5. The bottom graph in FIG. 6 represents the pulse window corresponding to the tertiary candidate peak at approximately 158 bpm as shown in FIG. 5. Note that in this instance, the tertiary candidate at frequency of 158 bpm has the lowest Pulse Window Confidence and no rejections based on calculated parameters. Note that FIGS. 4-6 are merely exemplary graphs illustrating sample calculations based on actual data obtained from typical pulse oximetry measurements The methods described above may be integrated into apparatuses and/or systems for calculating blood oxygen saturation. Referring to FIG. 7, one apparatus embodiment of this invention comprises a motion artifact rejection circuit card 10 with an I/O device 11, a processor 12 and memory 14 for storing a computer programmed algorithm for motion artifact rejection as described in the above methods. Processor 12 may be a digital signal processor. I/O device 11 may be any circuitry that allows communication to and from external circuitry, for example, and not by way of limitation, bus interface circuitry. I/O device 11 may include a circuit card edge connector for plugging into a pulse oximetry monitor system. Memory 14 may be any solid-state electronic memory suitable for storing digital data including, for example, computer code and measurement data.

I/O device 11 may include an interface for accepting a pulse-estimate input 30 from an external source 40. The pulse-estimate input 30 may be accepted in a wide range of formats. By way of example, and not limitation, the pulse-estimate input 30 may be a simple digital input indicating the current heart/pulse rate, a digital time-domain representation of a pulse/heart rate, and an analog time-domain representation of a pulse/heart rate. The digital time domain representation may be a representation that updates at a relatively high rate (e.g., 100 Hz) wherein the pulse is indicated by one, or a relatively small number of samples asserted, and the rest of the samples of the pulse period negated. The analog time domain representation may be a representation similar to those of the red and IR signals, which, when sampled by the I/O device 11, may subsequently be subject to the signal processing similar to that for the Red and IR signals.

The pulse-estimate input 30 may come from a wide variety of external sources 40. By way of example, and not limitation, the external source 40 may include an ECG, ultrasonic sensors, chest motion sensors, intra-arterial catheter, and the like.

Figure 7:
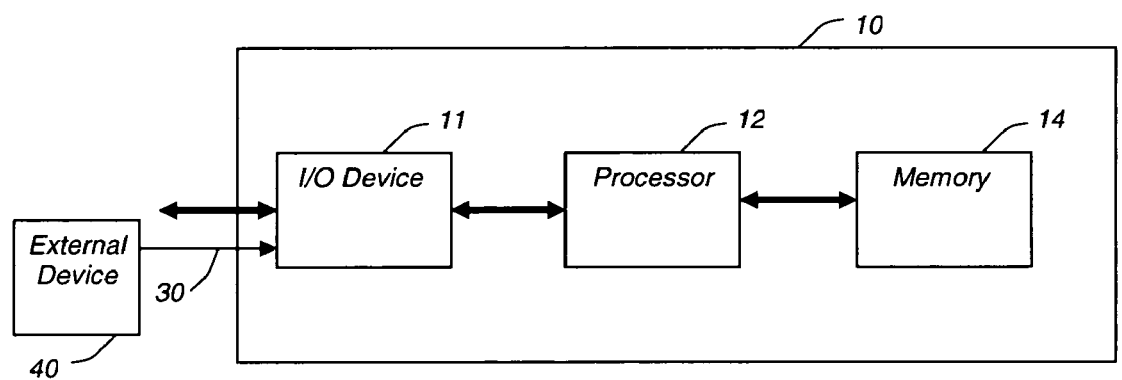
FIG. 7 is a block diagram of a motion artifact rejection circuit card configured to remove noise artifacts from signals representing bodily parameters in accordance with the invention.
Figure 8:
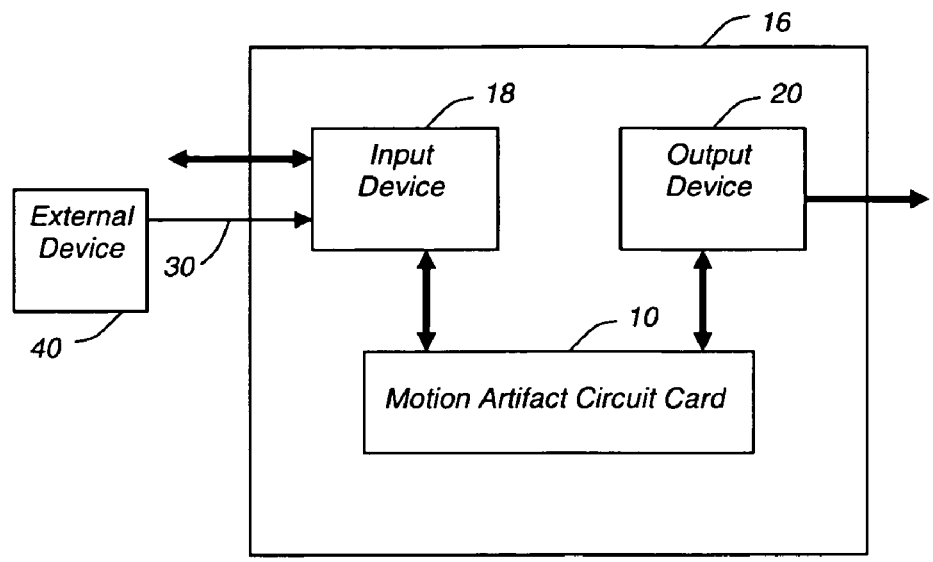
FIG. 8 is a block diagram of a pulse oximetry system including a motion artifact rejection circuit card capable of removing noise from pulse oximetry data in accordance with the invention.

Referring to FIG. 8, the motion artifact rejection circuit card 10 of FIG. 7 may be incorporated in a complete pulse oximetry system 16 for eliminating motion-induced noise artifacts in electrical signals (as described in the method embodiments above) and calculating and displaying physiological parameters, either as a discrete circuit card or as part of a larger circuit card, such as a motherboard, controlling other functions of the pulse oximetry system 16. The pulse oximetry system 16 also includes an input device 18 and an output device 20. Input device 18 may be a pulse oximeter sensor with red and IR LED light sources and a photodetector to convert transmitted or reflected light into an electrical signal. Input device 18 may also include the pulse-estimate input 30 from an external source 40 as explained above with reference to FIG. 7.

Output device 20 may be a display device such as a cathode ray tube device, liquid crystal display, active matrix display or any other suitable display device known to one of skill in the art. Alternatively, output device 20 may be a printer for producing a permanent or written record such as a laser printer, ink jet printer, thermal printer, dot matrix printer or any other suitable printer known to one of skill in the art. The pulse oximetry system 16 may be any pulse oximeter that uses the principles of operation as described above. A particular pulse oximeter for which the circuit card embodiment as described above is suitable for use is the Respironics, Inc. (formerly Novametrix Medical Systems, Inc.), Model 520A, Pulse Oximeter.

Figure 9:
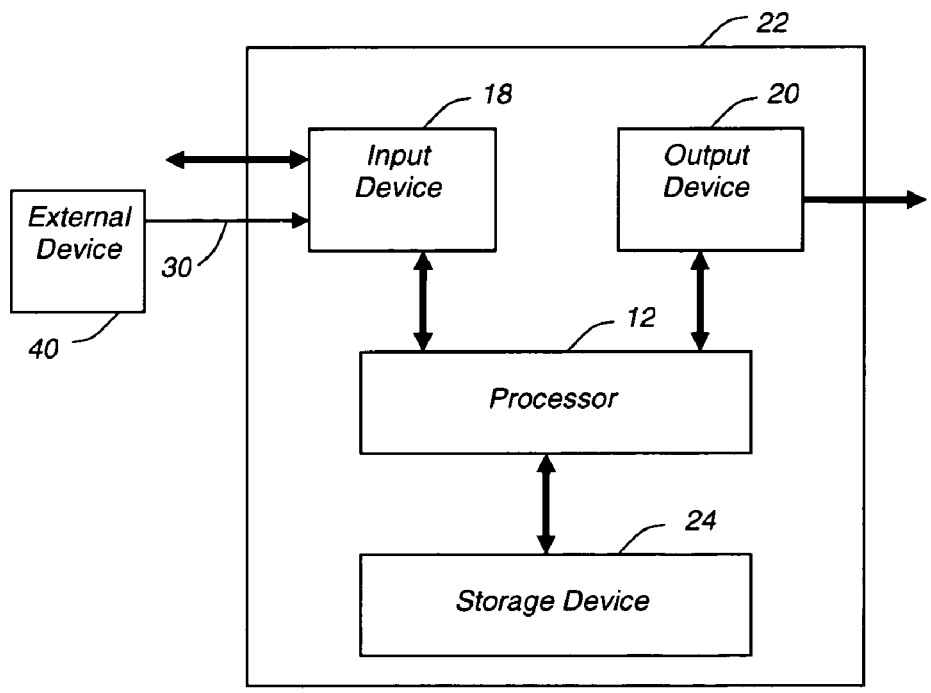
FIG. 9 is a block diagram of a pulse oximetry system including a processor device programmed to remove noise from pulse oximetry data in accordance with the invention.

Referring to FIG. 9, a block diagram of a pulse oximetry system 22 including a processor device 12, an input device 18, an output device 20 and a storage device 24, is shown. Input device 18 may be a pulse oximeter sensor with red and IR LED light sources and a photodetector to convert transmitted or reflected light into an electrical signal. Input device 18 may also include the pulse-estimate input 30 from an external source as explained above with reference to FIG. 7. Output device 20 may be a display device such as a cathode ray tube device, liquid crystal display, active matrix display or any other suitable display device known to one of skill in the art. Alternatively, output device 20 may be a printer for producing a permanent or written record such as a laser printer, ink jet printer, thermal printer, dot matrix printer or any other suitable printer known to one of skill in the art. Storage device 24 may be a disk drive, or any kind of solid-state electronic memory device suitable for storing digital data including, for example, computer code and measurement data.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of removing motion artifacts, comprising:
transforming a plurality of electrical signals representative of a plurality of attenuated light signals into frequency domain data;
identifying a plurality of candidate peaks from the frequency domain data;
eliminating candidate peaks from the plurality of candidate peaks such that no two of the plurality of candidate peaks comprise harmonics of one another;
filtering each of the plurality of candidate peaks;
accepting a pulse-estimate input;
developing selection parameters associated with each of the plurality of candidate peaks and the pulse-estimate input; and
selecting a best frequency from at least some of the plurality of candidate peaks and the pulse-estimate input by employing at least some of the selection parameters.

2. The method of claim 1, wherein selecting the best frequency comprises analyzing each of the plurality of candidate peaks and the pulse-estimate input with respect to at least some of the selection parameters to find the best frequency.

3. The method of claim 1, wherein identifying the plurality of candidate peaks further comprises:
assigning a largest power amplitude as a primary candidate peak;
assigning a next largest power amplitude as a secondary candidate peak; and
assigning a previous non-zero pulse rate as a tertiary candidate peak if the previous non-zero pulse rate is neither the primary candidate peak nor the secondary candidate peak.

4. The method of claim 1, wherein transforming the plurality of electrical signals is performed using a fast Fourier transform, a periodogram, a correlogram, an autoregressive methods, Prony's method, minimum variance methods, maximum likelihood methods, a discrete cosine transform, a wavelet transform, a discrete Hartley transform, or a Gabor transform.

5. he method of claim 1, further comprising conditioning the plurality of electrical signals to reduce spectral leakage prior to the transforming act.

6. The method of claim 1, wherein the filtering comprises using a narrow band filter;
using a narrow band filter with a variable center frequency;
using one of n narrow band filters to mask influence of candidate frequencies not under evaluation; or
using a narrow band filter, wherein filter coefficients are generated and adjusted so that a center frequency of the narrow band filter is approximately a center frequency associated with each of the candidate peaks.

7. The method of claim 1, wherein the selection parameters include at least one of: pulse width variability; $SpO_2$ variability; pulse window $SpO_2$; pulse peak amplitude variability; pulse rate history percentage; window pulse rate; and pulse window confidence.

8. The method of claim 1, wherein the selection parameters include at least one of:
pulse width variability calculated as a sum of absolute differences between individual pulse widths and an average pulse width normalized by the average pulse width;
$SpO_2$ variability calculated as a sum of absolute difference between individual $SpO_2$ values and an average $SpO_2$ for a given pulse window;
pulse window $SpO_2$ calculated by taking a measure of central tendency of all individual $SpO_2$ calculations in a given pulse window;
pulse peak amplitude variability calculated as a sum of differences between individual pulse peak amplitudes and average pulse peak amplitude for a given pulse window;
pulse rate history percentage calculated as a percentage of time that a pulse rate corresponding to a candidate peak has occurred in a given period of time;
pulse window confidence calculated as a weighted sum of pulse width variability, $SpO_2$ variability, pulse peak amplitude variability and pulse rate history percentage; and
window pulse rate calculated by dividing a sum of all pulse width times of all peaks in a data segment by a quantity of peaks detected in the data segment.

9. A method of determining parameters related to blood flow, comprising:
acquiring a segment of red data by transforming an electrical signal representative of an attenuated red light signal;
acquiring a segment of infrared data by transforming an electrical signal representative of an attenuated infrared light signal;
transforming the segment of red data and the segment of infrared data into red frequency domain data and infrared frequency domain data, respectively;
identifying a plurality of candidate peaks from the red frequency domain data and the infrared frequency domain data;
eliminating harmonic frequencies from the plurality of candidate peaks such that no two of the plurality of candidate peaks comprise harmonics of one another;
filtering each of the plurality of candidate peaks;
accepting a pulse-estimate input;
developing selection parameters associated with each of the plurality of candidate peaks and the pulse-estimate input;
selecting a best frequency from at least some of the plurality of candidate peaks and the pulse-estimate input by employing at least some of the selection parameters; and
repeating the above acts for a new segment of red data and a new segment of infrared data.

10. The method of claim 9, further comprising outputting at least one of a pulse rate, $SpO_2$, and a blood oxygen saturation, relating to the best frequency.

11. The method of claim 9, wherein selecting the best frequency comprises analyzing each of the plurality of candidate peaks and the pulse-estimate input with respect to at least some of the selection parameters to find the best frequency.

12. The method of claim 9, wherein the identifying the plurality of candidate peaks comprises:
assigning a largest power amplitude as a primary candidate peak;
assigning a next largest power amplitude as a secondary candidate peak; and
assigning a previous non-zero pulse rate as a tertiary candidate peak if the previous non-zero pulse rate is neither the primary candidate peak nor the secondary candidate peak.

13. The method of claim 9, wherein the selection parameters comprise at least one of:
  pulse width variability calculated as a sum of absolute differences between individual pulse widths and an average pulse width normalized by the average pulse width;
  $SpO_2$ variability calculated as a sum of absolute difference between individual $SpO_2$ values and an average $SpO_2$ for a given pulse window;
  pulse window $SpO_2$ calculated by taking a measure of central tendency of all individual $SpO_2$ calculations in a given pulse window;
  pulse peak amplitude variability calculated as a sum of differences between individual pulse peak amplitudes and average pulse peak amplitude for a given pulse window;
  pulse rate history percentage calculated as a percentage of time that a pulse rate corresponding to a candidate peak has occurred in a given period of time;
  pulse window confidence calculated as a weighted sum of pulse width variability, $SpO_2$ variability, pulse peak amplitude variability and pulse rate history percentage; and
  window pulse rate calculated by dividing a sum of all pulse width times of all peaks in a data segment by a quantity of peaks detected in the data segment.

14. A motion artifact analyzer comprising:
  (a) a processor for processing at least one computer program; and
  (b) a memory operably coupled to the processor and storing the at least one computer program, the at least one computer program including instructions for implementing a method of removing motion artifacts, the method comprising:
  (1) acquiring a segment of red data by transforming an electrical signal representative of an attenuated red light signal;
  (2) acquiring a segment of infrared data by transforming an electrical signal representative of an attenuated infrared light signal;
  (3) transforming the segment of red data and the segment of infrared data into red frequency domain data and infrared frequency domain data, respectively;
  (4) identifying a plurality of candidate peaks from the red frequency domain data and the infrared frequency domain data;
  (5) eliminating harmonic frequencies from the plurality of candidate peaks such that no two of the plurality of candidate peaks comprise harmonics of one another;
  (6) filtering each of the plurality of candidate peaks;
  (7) accepting a pulse-estimate input;
  (8) developing selection parameters associated with each of the plurality of candidate peaks and the pulse-estimate input;
  (9) selecting a best frequency from at least some of the plurality of candidate peaks and the pulse-estimate input by employing at least some of the selection parameters; and
  (10) repeating the above acts for a new segment of red data and a new segment of infrared data.

15. The motion artifact analyzer of claim 14, wherein selecting the best frequency comprises analyzing each of the plurality of candidate peaks and the pulse-estimate input with respect to at least some of the selection parameters to find the best frequency.

16. The motion artifact analyzer of claim 14, wherein the processor is a digital signal processor.

17. The motion artifact analyzer of claim 14, wherein the method further comprises calculating and outputting at least one of pulsatile blood oxygen concentration, $SpO_2$, and pulse rate, using the best frequency.

18. The motion artifact analyzer of claim 14, further comprising an external source operably coupled to the processor and configured for providing the pulse-estimate input.

19. The motion artifact analyzer of claim 14, further comprising a pulse oximeter including an input device and an output device.

20. The motion artifact analyzer of claim 19, wherein the method further comprises calculating and outputting a pulsatile blood oxygen concentration, $SpO_2$, a pulse rate, or both using the best frequency.

* * * * *